(12) United States Patent
Hodzic et al.

(10) Patent No.: US 7,637,144 B2
(45) Date of Patent: Dec. 29, 2009

(54) MEASURING DEVICE, PREFERABLY A TEST STAND FOR ENGINES AND VEHICLES FOR ANALYZING EXHAUST GASES OF A COMBUSTION ENGINE

(75) Inventors: Aden Hodzic, Graz (AT); Stefan Kerschbaumer, Graz (AT); Urs Gerspach, Graz (AT); Erich Schiefer, Graz (AT)

(73) Assignee: AVL List GmbH, Graz (AT)

( * ) Notice: Subject to any disclaimer, the term of this patent is extended or adjusted under 35 U.S.C. 154(b) by 182 days.

(21) Appl. No.: 10/579,970

(22) PCT Filed: Nov. 25, 2004

(86) PCT No.: PCT/AT2004/000413

§ 371 (c)(1),
(2), (4) Date: Mar. 7, 2007

(87) PCT Pub. No.: WO2005/052539

PCT Pub. Date: Jun. 9, 2005

(65) Prior Publication Data

US 2008/0022752 A1    Jan. 31, 2008

(30) Foreign Application Priority Data

Nov. 25, 2003    (AT)    ............... GM836/2003

(51) Int. Cl.
*G01N 33/00*    (2006.01)
(52) U.S. Cl. ..................................... 73/23.31
(58) Field of Classification Search .............. 73/23.31
See application file for complete search history.

(56) References Cited

U.S. PATENT DOCUMENTS 3,765,842 A * 10/1973 Purt .......................... 436/55

(Continued)

FOREIGN PATENT DOCUMENTS

DE    3642018    6/1987

(Continued)

OTHER PUBLICATIONS

U. Simon, "Gassensorik-Impedanzspektroskopie an Nanoporosen Feststoffen" in FB8-Inorganic Chemistry, at Hanover Trade Fair, 1966.

(Continued)

*Primary Examiner*—Daniel S Larkin
(74) *Attorney, Agent, or Firm*—Dykema Gossett PLLC

(57) ABSTRACT

The invention relates to a measuring device (1), preferably a test stand for engines and vehicles for analyzing exhaust gases of a combustion engine (2), comprising at least one exhaust gas supply line (3, 4), which can be connected to the exhaust system of the combustion engine (2) and which supplies at least one measuring branch (7, 8, 9) each provided with a respective analysis unit (12, 13, 14) for determining exhaust gas constituents. According to the invention, a filter device (16a to 16f) is provided in at least one cool measuring branch (9) upstream from the analysis unit (14) and/or between different components (14a, 14b) of the analysis unit (14) and/or on the output side of at least one analysis unit (12, 13, 14) of one of the measuring branches (7, 8, 9). This filter unit contains a filter material that is selective with regard to gaseous hydrocarbons, preferably a filter material selected from the group consisting of zeolites and/or silicates.

12 Claims, 3 Drawing Sheets

U.S. PATENT DOCUMENTS

| | | | | |
|---|---|---|---|---|
| 3,927,979 | A * | 12/1975 | Byrne et al. | 436/134 |
| 4,678,568 | A * | 7/1987 | Goldman et al. | 210/167.23 |
| 5,340,388 | A * | 8/1994 | Breton et al. | 106/31.32 |
| 5,690,099 | A * | 11/1997 | Abramov et al. | 128/202.26 |
| 5,804,155 | A | 9/1998 | Farrauto et al. | |
| 5,969,623 | A * | 10/1999 | Fleury et al. | 340/632 |
| 6,159,363 | A | 12/2000 | Collins et al. | 210/136 |
| 6,862,927 | B2 * | 3/2005 | Craig et al. | 73/114.69 |
| 6,908,558 | B2 * | 6/2005 | Stinson et al. | 210/660 |
| 6,939,396 | B2 * | 9/2005 | Petersson et al. | 96/130 |
| 2001/0054309 | A1 | 12/2001 | Ohmori et al. | |

FOREIGN PATENT DOCUMENTS

| | | | |
|---|---|---|---|
| DE | 3812417 A * | 10/1989 | |
| DE | 19607506 | 9/1997 | |
| DE | 20200373 | 6/2002 | |
| EP | 0414446 | 2/1991 | |
| EP | 632263 * | 1/1995 | 73/23.31 |
| EP | 0848250 | 6/1998 | |
| EP | 0880022 | 11/1998 | |
| EP | 0894950 | 2/1999 | |
| JP | 2002257773 A | 9/2002 | |

OTHER PUBLICATIONS

English Abstract of JP 2002257773.
English Abstract of DE 19607506.
English Abstract of DE 3642018.

* cited by examiner

MEASURING DEVICE, PREFERABLY A TEST STAND FOR ENGINES AND VEHICLES FOR ANALYZING EXHAUST GASES OF A COMBUSTION ENGINE

BACKGROUND OF THE INVENTION

1. Field of the Invention

The invention relates to a measuring device, preferably a test stand for engines and vehicles for analyzing exhaust gases of a combustion engine, comprising at least one exhaust gas supply line which can be connected to the exhaust system of the combustion engine and which supplies at least one measuring branch each provided with at least one analysis unit each for determining exhaust gas constituents.

2. The Prior Art

The combustion of hydrocarbon compounds (fuels) in the internal combustion engine together with air components leads to combustion products such as CO, $H_xC_y$, $NO_x$ and exhaust particulates as limited components for engines and vehicles as determined in the currently valid laws on the one hand and to $N_2$, $H_2O$, $CO_2$ and $O_2$ as non-limited components. Additionally there are trace elements and impurities of the fuel such as sulfur, etc.

The potential further development of drive technology progresses into technological regions—driven, among other things, by increasingly stricter legal limitations imposed on the exhaust gas limit values—in which combustion effects occur which up until now only occurred in vehicles singularly in the research area or in extreme applications. As a result of stratification of fuel, special injection techniques, exhaust gas aftertreatment systems etc. for example there is a very complex interaction process in the combustion chamber, as also in the downstream elements of the process chain, the exhaust gas aftertreatment, exhaust gas measurement, etc.

Further parameters to be taken into account in the exhaust gas measurement are the humidity, temperature and ambient pressure. Humidity in the exhaust gas depends on the fuel, the combustion process and the atmospheric moisture. The exhaust temperature reaches approx. 600° C. and higher in the exhaust system. The measuring temperature as required by law for exhaust gas measurement technology is 191° C. The pressure in the exhaust cycle can be subject to strong changes depending on the type of engine and the load behavior. Furthermore, the ambient pressure depends on the altitude.

A major problem is the soiling of the exhaust gas measuring device and its analysis units by deposits of the exhaust gases, for which mainly the HC components and their decay products are responsible. A further problem for the operators and the ambient environment is the exhaust air of engine and vehicle test stands.

From DE 202 00 373 U1 (ENOTEC GmbH) a measuring probe is known for measuring $O_2$ and CO in hot flue gases. A measuring probe tube comprises in its region situated in a flue gas channel a substantially cylindrically arranged measuring chamber which is sealed off by a gas-permeable filter. A heated $O_2$-sensor and a CO-sensor are arranged in the measuring chamber so close to one another that the heat generated by the $O_2$-sensor encloses the CO-sensor.

A method and an apparatus for gas analysis is described in EP 0 414 446 A2 (ENGINE TEST TECHNIQUE LIMITED). The gas to be analyzed is taken from the exhaust gas train of an internal combustion engine and is guided with the help of a pump via a first filter to a chamber which may comprise a second filter. The gas to be analyzed is supplied thereafter to a measuring cell in which optical gas analysis is carried out by means of infrared radiation, with the concentration of CO, $CO_2$ and hydrocarbons being determined.

It is further known from JP 2002-257773A (NGK INSULATORS LDT) to provide a filter unit for a gas sensor arranged in a metal tube, which filter unit can be attached to the end of the metal tube in a detachable fashion.

In an article of the University GH Essen by Dr. Ulrich Simon ("Gassensorik—Impedanzspektroskopie an nanoporösen Feststoffen; "Gas sensory analysis—Impedance spectroscopy on nano-porous solids"), exponate of the "FB8—Inorganic chemistry" at the Hanover Trade Fair 1996, chemical gas sensors are described for measuring gas concentrations in motor-car exhaust gases, using non-porous solids as gas-sensitive materials. A few milligrams of a nano-porous solids such as zeolite, are applied in a thin layer of only a few hundredth of millimeters onto an electronic chip structure, in a so-called interdigital condenser, and the electric properties are measured.

SUMMARY OF THE INVENTION

It is the object of the present invention to improve a known measuring device for analyzing exhaust gases of an internal combustion engine, preferably a test stand for engines and vehicles, in such a way that deposits of exhaust gases reducing the quality of the measurement and leading to soiling of the exhaust gas measuring device can be avoided or substantially reduced. Measures shall further be taken in order to reduce the burden on the environment and the operators by the exhaust air of such measuring devices.

This object is achieved in accordance with the invention in such a way that a filter device is provided in at least one cool measuring branch upstream of the analysis unit and/or between different components of the analysis unit and/or on the output side of at least one analysis unit of one of the measuring branches, which filter unit comprises a filter material that is selective with regard to gaseous hydrocarbons. It is especially provided that the filter device contains a filter material selected from the group consisting of zeolites and/or silicates. By filtering the reactands and the described mechanisms in the gaseous phase, solid and liquid deposits in the downstream components are prevented. Deposits are prevented by continuous heating in the hot measuring branches, so that no filter is necessary here at least before the analysis units.

Especially for the use of the filter device in accordance with the invention on the input side of an analysis unit it is important that the gas constituents to be measured, such as CO, $CO_2$ and/or $O_2$, are not impaired to the highest possible extent by the filter material. It has been noticed surprisingly that naturally occurring or chemically purified or adapted zeolites or zeolite-like materials are outstandingly suitable as filter materials. For example, so-called "Eisenberger mass" can be used as a filter material which is principally composed of the following components:

| | | |
|---|---|---|
| $SiO_2$: 87.7% | CaO: 1.7% | $TiO_2$: 0.3% |
| $Al_2O_3$: 4.8% | MgO: 0.7% | |
| $Na_2O$: 3:9% | $K_2O$: 0:5% | |

In accordance with the invention, the adsorption material can be present as a granulate with a grain size of up to 30 mm, preferably 4 mm to 10 mm.

From the analyses with the help of mass spectrometers, the large variety of the mechanisms can be seen, whose effects are responsible for the precipitation of HC components in the measuring devices. The adsorption (or occlusion) is a relevant factor. The effect comprises both chemical as well as physical reaction mechanisms, with Van der Waals forces, electrostatic forces and valence forces being responsible for the description of the interaction at the interphase between solid body and gas phase. The reaction occurs both in the gas phase as well as in the solid body phase.

As a result of the presence of $O_2$, NO and $NO_2$, the reactions are changed in a gas-catalytic respect. Similarly, the electric potentials between gas and the solid body change subsequently, so that the catalytic effect can occur spontaneously in an accelerated manner on the activated ionic and anionic centers of the solid body phase. The entire reaction time thus depends on the size of the surface. Carboxylic acid esters, ketones, alcohols and other compound classes originate spontaneously at the surface during the reaction. Within the progress of the reaction, the saturation vapor pressure is fallen below, whereupon condensation occurs. Whereas the condensation coefficient changes only slightly with the covering, the adhesion coefficient begins to drop with alternating covering. The reaction rate is influenced by the composition of the exhaust gas and is composed of condensation, adhesion coefficient, catalytic reaction rate and spontaneous polymerization.

Catalytic reactions can occur within the pores of the filter material. Catalytically active are the acid centers of the zeolite structure and/or noble metals introduced into the zeolites, e.g. platinum. The chemical selectivity of the process and the form selectivity with regard to the reactands and the transitional state are relevant for the reaction speed.

In accordance with the invention, the filter device can be arranged upstream or above an exhaust gas cooling device provided upstream of the analysis unit, so that the transport of condensate obtained in the filter device preferably occurs by gas flow and/or gravity in the direction of the exhaust gas cooling device. The condensate from the filter can then advantageously be disposed of together with that of the cooling device. The following applications can be considered:

A) Application for Filtering Exhaust Gas in Exhaust Gas Measuring Systems.

The filtering is performed for protecting measuring instruments and sensor devices in the analysis unit. For research and development, the engine is often operated at operating points in which combustion occurs in an impure manner and thus releases pollutants which are rarely released in normal use. These substances are mostly toxic and carcinogenic. Certain exhaust gas components lead in the measuring systems to aromatic and chain-like agglomerates which soil the systems, cause blockages and serious damage to the systems. The cleaning of such highly condensing polymers is very difficult. Spontaneous polymerization occurs in the filter in accordance with the invention as a result of the catalytic effect, as a result of which the contamination of the measuring device can substantially be prevented.

The use of adsorption filters was prohibited by law until now for the certification of vehicles, because it was generally believed that such filters should reduce the component CO for example which is limited by law. Tests have shown however that the filter materials in accordance with the invention contradict this bias. The influence of such filters for the limited exhaust gas component remains within the precision required for the measuring instrument and thus technically meets the requirements for certification. A built-in filter offers protection also in the case of the ignition of a combustible mixture in the region of the sensor devices because the pressure wave is intercepted by the filter and the flame front is extinguished in the filter. The loaded zeolite can be regenerated at temperatures over 500° C. The regeneration can be realized with a hot air flow through the filter.

B) Selective Measurement of Gas Components

With the help of a selective adsorption of individual gas components (e.g. $H_2SO_4$) it is possible to remove components from the exhaust gas stream to be measured with the help of zeolites or zeolite-like materials. Cross-sensitivities of water or sulfur, for example, can thus be eliminated. A further measuring principle is obtained in such a way that even the adsorbed quantity of a certain gas component in the filtering column is a measure for its gas concentration. The composition of the deposit can be determined from respective analyses of the filtrate. The exhaust gas concentration of such gas components can thus be measured by means of respective detectors with the help of zeolite or zeolite-like material.

In accordance with a further development of the invention, the filter device can be arranged on the output side of at least one measuring branch of the measuring device. It is thus possible to arrange each of the measuring branches on the output side with a separate filter device or to combine the individual measuring branches on the output side and to provide a common, respectively dimensioned filter device in the exhaust air line of the test stand. This leads to the following applications:

C) Filtering of the Test Stand Air for Protecting the Operators and the Environment.

The contamination with hazardous exhaust gases is problematic especially in development and research test stands for engine development. This concerns the environment on the one hand, and the staff on the other hand. The composition of the exhaust gas and the application duration of the pollutants on the staff have an adverse effect on health. The originating exhaust gas components can have toxic or mutagenic effects in their local concentration. The employed zeolite or zeolite-like filter materials very rapidly adsorb hydrocarbons, fuel vapors and other pollutants from the exhaust air in test stands. The health hazard is thus minimized and the working quality for the operating staff is improved substantially. Previously, such exhaust gases were guided in an unfiltered manner to the ambient environment.

The filter device described above which contains a filter material from the group of the zeolites and/or the silicates is also suitable for cleaning and conditioning intake and diluent air for exhaust gas analysis.

In the case of exhaust gas measuring devices which admix a defined quantity of diluent air to the exhaust gas prior to measurement precise exhaust gas measurements can be distorted in such a way that already the diluent air contains pollutants which have an influence on the result of the measurement.

Filters with zeolites and/or zeolite-like materials can therefore be used for applications for filtering and conditioning the intake and/or diluent air for exhaust gas measuring devices. The zeolite filters are comparatively inexpensive as compared with conventionally used hepar and carbon filters and are superior to the same in respect of their efficiency. The zeolite filter removes undesirable gas components from the diluent air (e.g. HC), as a result of which the measuring method is simplified substantially. The analytic system for measuring gas situated behind the filter is practically not influenced by the filtering. The mentioned materials are similarly suitable to condition the air concerning temperature and humidity content. Especially for applications in so-called SULEV (Super Ultra Low Emission Vehicles) measuring systems (and lower concentrations), zeolite or zeolite-like materials can be used with considerable advantages in respect of technology and cost-effectiveness.

The above filter device which contains a filter material from the group of zeolites and/or silicates is further suitable as an accessory device for removing toxic components from the exhaust gas of internal combustion engine which may occur according to commonly used exhaust gas aftertreatment systems.

Depending on the operating state of the combustion engine, especially an internal combustion engine, new toxic substances such as Nitro-PAHs (polycyclic aromatic hydrocarbons) can be formed from the present non-combusted hydrocarbons and nitrogen oxides in the exhaust gas system. Previously used apparatuses for exhaust gas cleaning of internal combustion engines contain noble metals such as platinum, palladium and rhodium for catalytic oxidation of CO and HG. The oxidation effect of these apparatuses is sufficient in order to fall below the statutory limit values, but are not sufficiently selective in order to totally eliminate these toxic components. On the contrary, the formation of such substances can even be promoted by the catalytic effect. Further hazardous compounds can originate from fuel additives.

This critical emission can be prevented by arranging a zeolite filter at the end of the exhaust gas system, in the direction of flow after the conventional exhaust gas aftertreatment. The zeolite filter is characterized by its ability to allow the adsorption of nitroaromatics and similar substances already at low temperatures and to desorb the same only at temperatures >600° C., as do not typically occur at the place of installation. It is possible to regenerate the loaded adsorber outside of the exhaust gas train. The low concentration of toxic substances in the exhaust gas allows long service intervals (service life) at acceptable additional volume and weight.

In accordance with the invention, the filter device can consist of a disposable cartridge, a cartridge with a refill set or a refillable cartridge which contains the filter material as a pourable material. In order to keep the abraded parts of the zeolite granulate from the analysis units, the cartridge may comprise a dust filter at least on the output side.

Zeolites or zeolite-like materials were used before especially for water conditioning and as builders in detergents and pharmaceuticals and cleaning agents. As is shown in EP 0 866 218 A1 for example, zeolites are also used as a structural material for adsorber-catalyst combinations for internal combustion engines and, according to DE 100 36 794 A1, as a base material for building $NO_x$ storage catalysts. As selective adsorbers, these materials are known in chemistry as carrier materials of chromatographs. Such substances are used in the laboratory for regulating humidity. Special substance design allows further the selective reactivity of these substances with certain molecules. This property is used especially for experiments with biogenic mechanisms and micro-organisms.

The invention is now explained in closer detail by reference to the schematic drawing.

DETAILED DESCRIPTION OF THE PREFERRED EMBODIMENTS

Figure 1:
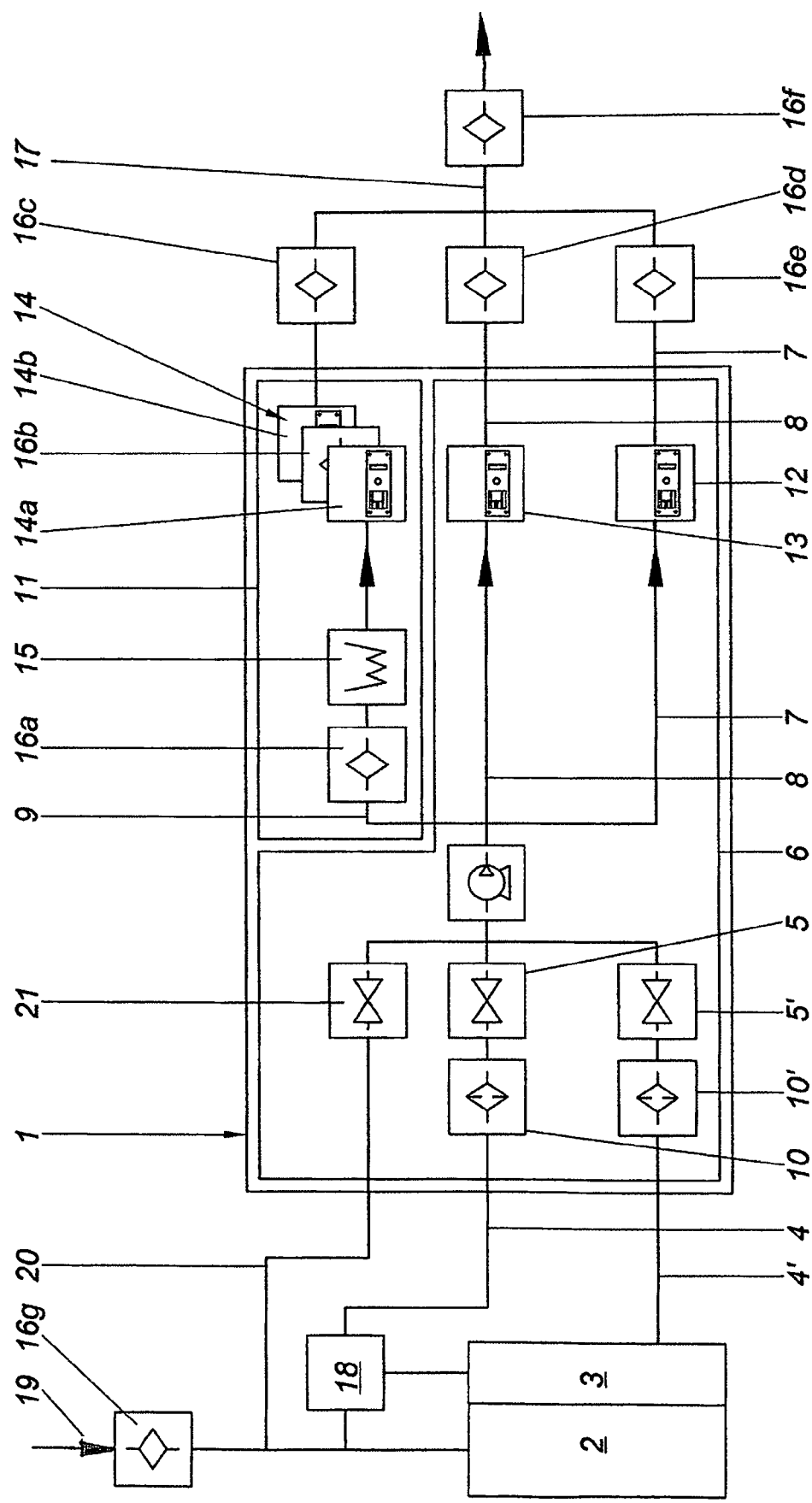
FIG. 1 shows a measuring device in accordance with the invention, preferably a test stand for engines and vehicles for analyzing the exhaust gases of an internal combustion engine.

The measuring device 1 as shown in FIG. 1 is used for analyzing the exhaust gases of an internal combustion engine 2 which is arranged on an engine test stand (not shown in closer detail). The measuring device 1 comprises two gas supply lines 4 and 4' which can be connected with different measuring points in the exhaust gas system 3 of the internal combustion engine 2 and which can be switched to the parallel measuring branches 7, 8 and 9 via valves 5 and 5'. On the input side of the valves 5 and 5', conventional particle filters 10 and 10' are arranged in the exhaust gas supply lines 4 and 4'. The measuring branches 7 and 8 are thermo-statisized to a measuring temperature of 191° C. in the schematically enhanced unit 6, with the measuring branch 7 comprising an analysis unit 12, for example, for determining NO and $NO_x$, and with the measuring branch 8 comprising an analysis unit 13 for determining the hydro-carbons.

The measuring branch 9 (see area 11 of the measuring device 1) is a cool measuring branch with a cooling device 15 which cools the exhaust gas stream especially for condensation of $H_2O$ to temperatures of between approx. 2° C. to 7° C. A filter device 16a is situated upstream of the exhaust gas cooling device 15, which filter device contains a filter material which is selective to gaseous hydrocarbons, as a result of which the subsequent analysis unit 14 and its components 14a and 14b can be kept completely free from deposits caused by polymerization, condensation, crystallization, etc., from gaseous source materials, especially hydrocarbons. The filter device 16a comprises a filter material of the group of zeolites and/or silicates and is provided upstream of a analysis unit 14, e.g. for determining the content of CO, $CO_2$ and/or $O_2$.

As is shown in FIG. 1, the filter device 16a can be arranged upstream of an exhaust gas cooling device 15 upstream of an analysis unit 14, so that the transport of condensate originating in the filter device 16a preferably occurs by the gas flow in the direction of the exhaust gas cooling device 15. It is also possible to arrange the filter device 16a above the exhaust gas cooling device 15, so that the transport of the obtained condensate preferably occurs by gravity in the direction of the exhaust gas cooling device 15. Both effects can be combined effectively by a respective arrangement above and upstream of the cooling device 15. The condensate can then easily be removed by suction with the help of a hose pumps, for example jointly with the condensate originating in the cooling device.

It is also possible to provide a filter device 16b which is an integral component of the analysis unit 14 and is arranged for example between different components 14a, 14b of the analysis unit 14.

As is further shown in FIG. 1, such filters 16c through 16e with zeolite as a filter material can also be arranged for filtering the test stand gases on the output side of the individual measuring branches 7 to 9 for the protection of the operating staff or in a collecting line 17 which leads together the measuring branches 7 to 9 on the output side of the measuring device.

As is further shown in FIG. 1, such filters 16c through 16f with zeolite as a filter material can also be arranged for filtering the test stand gases on the output side of the individual measuring branches 7 to 9 for the protection of the operating staff or in a collecting line 17 which leads together the measuring branches 7 to 9 on the output side of the measuring device.

The exhaust gas measuring device 1 can also comprise a device 18 with which the exhaust gas is admixed with a predefined quantity of diluent air prior to the measurement. In order to avoid distortions in the results of the measurement, a filter device 16g with a filter material of the group of zeolites and/or silicates can also be arranged in the supply line 19 for the diluent air or for the intake air of the internal combustion engine. The filtered intake air can be supplied for calibration purposes for example, via a separate feed line 20 and the valve 21 into the individual measuring branches 7, 8, 9.

Figure 2:
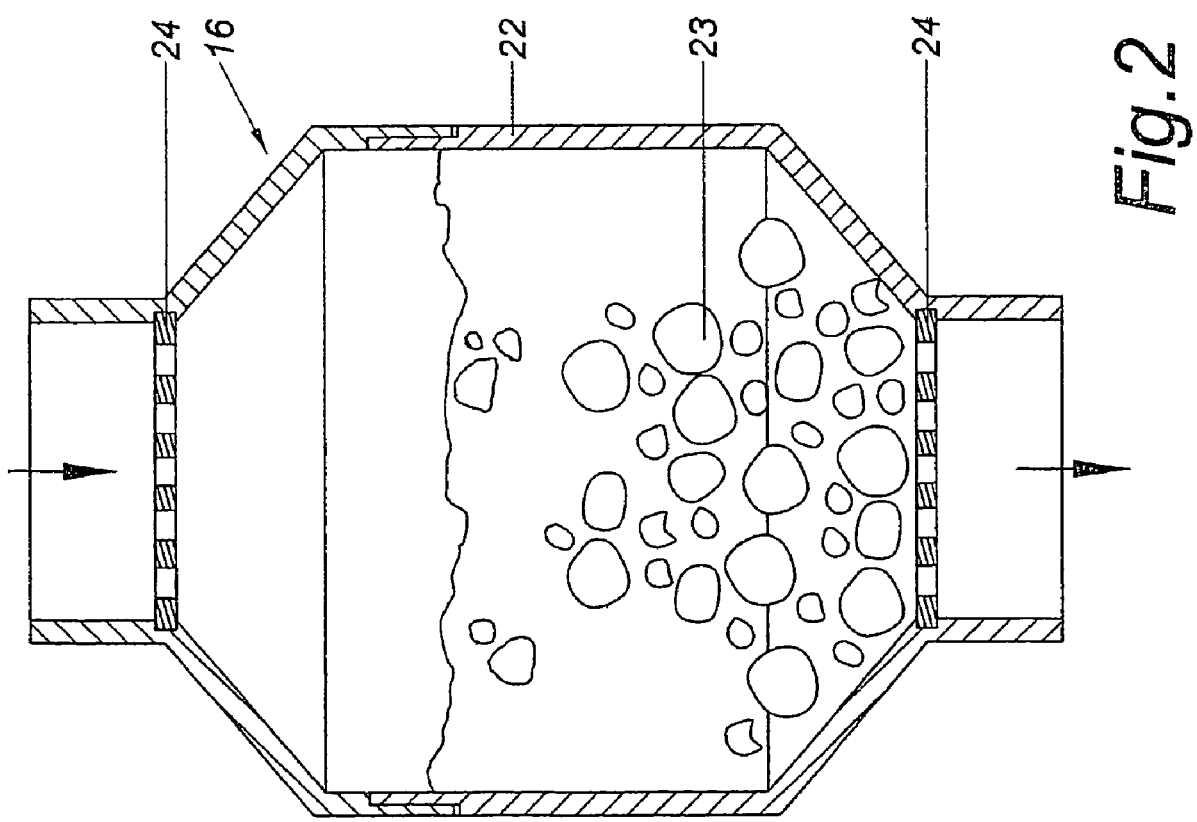
FIG. 2 shows an embodiment of a filter device of the measuring device according to FIG. 1.

FIG. 2 shows a sectional view of the filter device 16a through 16g of the measuring device according to FIG. 1 which consists of a cartridge 22 containing the filter material 23 as a pourable material. Dust filters 24 are arranged on the input and output side of the cartridge 22. The filter material can also be offered in the form of a refill set or the entire filter unit as a disposable cartridge.

Figure 3:
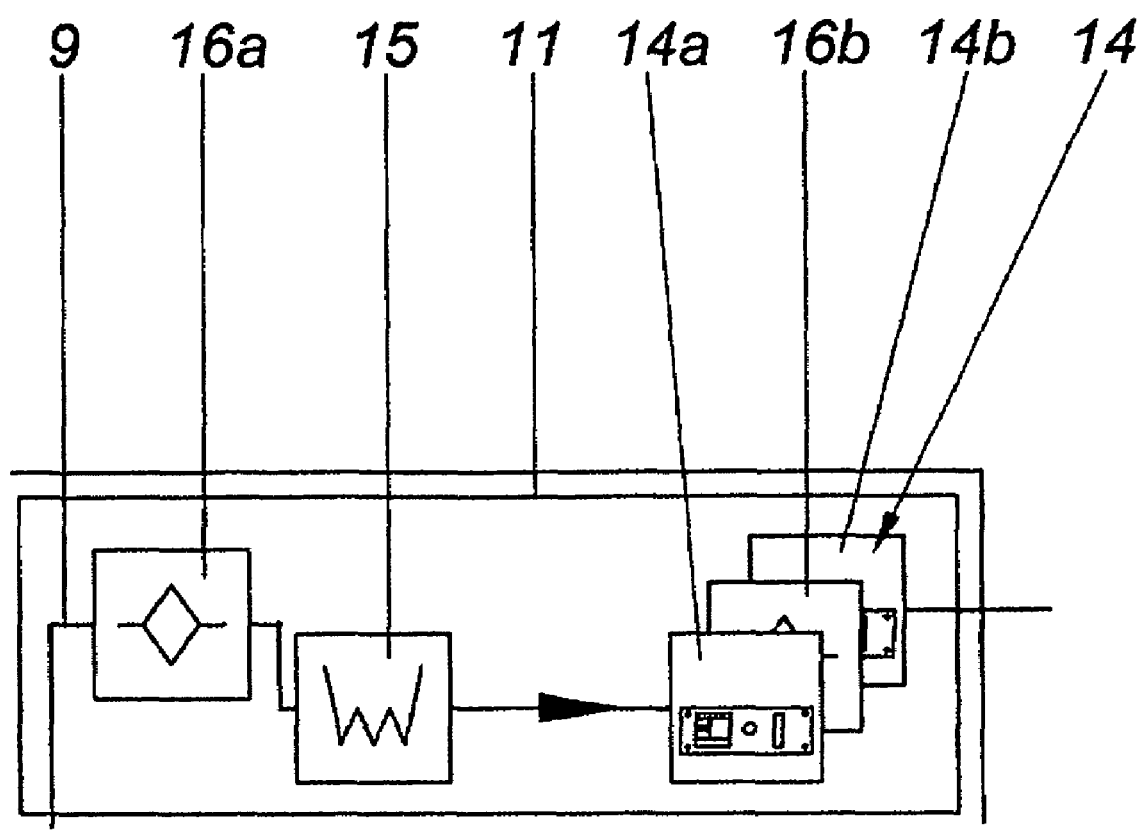
FIG. 3 shows a variant of a portion of the measuring device of FIG. 1 when the filter device is located above the exhaust gas cooling device.

FIG. 3 shows a variant of FIG. 1 wherein the filter device 16a is located above the exhaust gas cooling device 15.

The invention claimed is:

1. A measuring device for analyzing exhaust gases of a combustion engine, comprising at least one exhaust gas supply line which is connectable to the exhaust system of the combustion engine and which supplies at least one measuring branch, each provided with at least one analysis unit for determining exhaust gas constituents, wherein a filter device is provided in at least one cool measuring branch upstream of the at least one analysis unit and/or between different components of the at least one analysis unit and/or on the output side of at least one analysis unit of one of the measuring branches, which filter device comprises a filter material that is selective with regard to gaseous hydrocarbons, wherein the filter device is arranged upstream of an exhaust gas cooling device upstream of the least one analysis unit, so that the transport of condensate originating in the filter device occurs by the gas flow in the direction of the exhaust gas cooling device.

2. A measuring device for analyzing exhaust gases of a combustion engine, comprising at least one exhaust gas supply line which is connectable to the exhaust system of the combustion engine and which supplies at least one measuring branch, each provided with at least one analysis unit for determining exhaust gas constituents, wherein a filter device is provided in at least one cool measuring branch upstream of the at least one analysis unit and/or between different components of the at least one analysis unit and/or on the output side of at least one analysis unit of one of the measuring branches, which filter device comprises a filter material that is selective with regard to gaseous hydrocarbons, wherein the filter device is arranged above an exhaust gas cooling device provided upstream of the at least one analysis unit, so that the transport of condensate originating in the filter device occurs by gravity in the direction of the exhaust gas cooling device.

3. The measuring device according to claims 1 or 2, wherein the filter device contains a filter material selected from a group consisting of zeolites and silicates.

4. The measuring device according to claims 1 or 2, wherein the filter device is an integral component of the analysis unit.

5. The measuring device according to claims 1 or 2, wherein the filter device is arranged on an output side of at least one of the measuring branches of the measuring device.

6. The measuring device according to claims 1 or 2, wherein the filter material is a granulate with a grain size of up to 30 mm.

7. The measuring device according to claims 1 or 2, wherein the filter material is a granulate with a grain size between 4 mm and 10 mm.

8. The measuring device according to claims 1 or 2, wherein the analysis unit of the at least one cool measuring branch comprises sensor devices for determining the CO, $CO_2$ and/or $O_2$ content of the exhaust gas.

9. The measuring device according to claims 1 or 2, wherein said measuring device is a test stand for engines and vehicles.

10. A measuring device for analyzing exhaust gases of a combustion engine, comprising at least one exhaust gas supply line which is connectable to the exhaust system of the combustion engine and which supplies at least one measuring branch, each provided with at least one analysis unit for determining exhaust gas constituents, wherein a filter device is provided in at least one cool measuring branch upstream of the at least one analysis unit and/or between different components of the at least one analysis unit and/or on the output side of at least one analysis unit of one of the measuring branches, which filter device comprises a filter material that is selective with regard to gaseous hydrocarbons, wherein the filter device is arranged upstream of an exhaust gas cooling device upstream of the at least one analysis unit, so that the transport of condensate originating in the filter device occurs by the gas flow in the direction of the exhaust gas cooling device, and wherein the filter device consists of a disposable cartridge, a cartridge with a refill set or a refillable cartridge.

11. A measuring device for analyzing exhaust gases of a combustion engine, comprising at least one exhaust gas supply line which is connectable to the exhaust system of the combustion engine and which supplies at least one measuring branch, each provided with at least one analysis unit for determining exhaust gas constituents, wherein a filter device is provided in at least one cool measuring branch upstream of the at least one analysis unit and/or between different components of the at least one analysis unit and/or on the output side of at least one analysis unit of one of the measuring branches, which filter device comprises a filter material that is selective with regard to gaseous hydrocarbons, wherein the filter device is arranged above an exhaust gas cooling device provided upstream of the at least one analysis unit, so that the transport of condensate originating in the filter device occurs by gravity in the direction of the exhaust gas cooling device, and wherein the filter device consists of a disposable cartridge, a cartridge with a refill set or a refillable cartridge.

12. The measuring device according to claims 10 or 11, wherein the cartridge comprises a dust filter at least on the output side.

* * * * *